United States Patent [19]

Zackheim et al.

[11] 4,385,052

[45] May 24, 1983

[54] USE OF TRIALKYLSILYL-6-AMINONICOTINA-MIDES FOR THE TREATMENT OF PSORIASIS

[75] Inventors: Herschel S. Zackheim; Raphael Pappo, both of Redwood City, Calif.

[73] Assignee: International Plant Research Institute, Inc., San Carlos, Calif.

[21] Appl. No.: 284,903

[22] Filed: Jul. 20, 1981

[51] Int. Cl.$^3$ .............................................. A61K 31/695
[52] U.S. Cl. .................................... 424/184; 424/266; 546/14
[58] Field of Search ................... 424/184, 266; 546/14

[56] References Cited

U.S. PATENT DOCUMENTS

| | | | |
|---|---|---|---|
| 3,781,291 | 12/1973 | Sulzbach et al. | 546/14 |
| 4,067,975 | 1/1978 | Yu et al. | 424/240 |
| 4,311,695 | 1/1982 | Starch | 424/184 |

OTHER PUBLICATIONS

Merck Index, 9th ed., #9741, (1976).

*Primary Examiner*—Leonard Schenkman
*Attorney, Agent, or Firm*—Townsend and Townsend

[57] ABSTRACT

The use of a composition for relieving the symptoms of psoriasis in humans is disclosed. The composition is an N-trialkylsilyl-substituted 6-aminonicotinamide. The composition is applied in a suitable pharmaceutical base, such as a cream or ointment, to the affected area of skin.

9 Claims, No Drawings

USE OF TRIALKYLSILYL-6-AMINONICOTINAMIDES FOR THE TREATMENT OF PSORIASIS

BACKGROUND OF THE INVENTION

1. Field of the Invention

This invention relates to the use of trialkylsilyl-6-aminonicotinamides for the treatment of psoriasis through topical application to improve and heal the skin lesions of psoriasis in humans.

2. Description of the Prior Art

Psoriasis is a chronic disease, and remains a disfiguring and disabling cutaneous impairment to millions of persons. Its etiology is completely unknown, and therefore, prevention remains inconceivable. Therapy has necessarily been empiric, and has included the systemic use of anti-mitotic drugs such as methotrexate to induce remissions of the lesions. However, acute and chronic toxicity on tissues other than skin has discredited use of methotrexate. Therefore, it is imperative that other means of therapy be found for external delivery of drugs so that toxicity is confined chiefly to the skin, or by the discovery of new drugs having nontoxic attributes.

U.S. Pat. No. 4,067,975 discloses the treatment of psoriasis with a family of 6-substituted nicotinamides, 6-substituted nicotinic acid and esters thereof and 2-substituted pyrazinamide or thionicotinamide. While such compounds have proven effective, their use must be accompanied by the application of Vitamin $B_3$ to avoid possible hearing impairment in the patient.

U.S. Pat. No. 3,920,840 discloses the treatment of psoriasis with one of the degradation products of mechlorethamine hydrochloride, N-methyldiethanolamine, a compound which is not primarily either antimitotic nor allergic.

SUMMARY OF THE INVENTION

Certain substituted 6-aminonicotinamides have now been discovered that are particularly useful in the treatment of psoratic conditions, without the type of toxic affects caused by prior art compounds.

The compounds useful in the method of this invention are N-trialkylsilyl-substituted 6-aminonicotineamides, substituted at other than the annular nitrogen. Either one, or both, of the hydrogen atoms in either, or both, of the amino groups may be replaced by a trialkylsilyl moiety. It is preferred that the total number of carbon atoms in the alkyls be 24 or fewer and more preferred that each alkyl include 4 or fewer carbon atoms. While up to four trialkylsilyl groups can be substituted (i.e., two at each non-annular nitrogen), it is preferred to include only a single trialkylsilyl group at each nitrogen.

The substituted 6-aminonicotinamides of this invention are particularly advantageous because of their lower toxicity and greater solubility, particularly when utilized in a topical application as part of a solution, an ointment or a lotion.

DESCRIPTION OF THE SPECIFIC EMBODIMENT

The substituted 6-aminonicotinamides of the present invention are those having the formula:

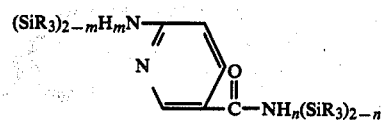

The trialkylsilyl groups $(SiR_3)$ each contain three alkyl groups (R) which may or may not have the same structure. It is preferred that the total number of carbon atoms in all three alkyl groups not exceed 24. It is more preferred that the alkyl groups be selected from methyl, ethyl, propyl, isopropyl, butyl, isobutyl and tert-butyl.

The compound may contain from one to four trialkylsilyl groups on the two non-annular nitrogens. Thus, both n and m are selected from the group 0, 1 and 2. While either m or n is always at least 1, it is preferred that both m and n be equal to 1, i.e., the compound includes one trialkylsilyl group on each of the two nitrogens.

1. Preparation of the Compounds

The compounds of the present invention may be prepared in accordance with the following equations:

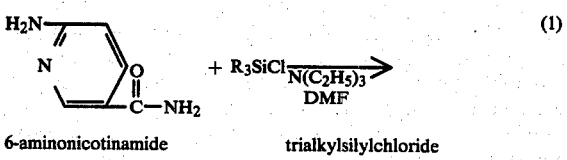

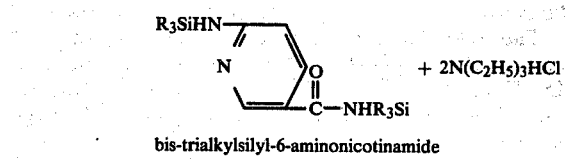

In equation (1), 6-aminonicotinamide is dissolved in dry DMF by heat and allowed to cool. While still warm, triethylamine is added and the resulting solution cooled. After cooling, the triethylchlorosilane is added and the solution is left to stand for a number of hours, typically overnight. The solution is then dried and the product removed by conventional means.

The bis-trialkylsilyl-6-aminonicotinamide obtained by equation (1) may be further reacted in the presence of a strong base, typically butyl lithium, to obtain a fully substituted compound as shown in equation (2). Of course, by limiting the amount of reactants, a compound substituted at only three of the four locations will be obtained.

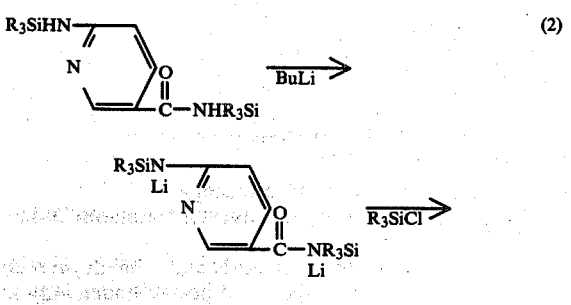

-continued

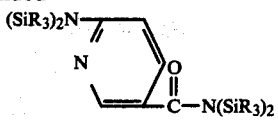

2. Preparation of the Therapeutic Compositions

The compounds of the present invention are admixed in a conventional manner with commonly available bases such as alcohols, creams or ointments. Both dimethyl sulfoxide (DMSO) and hydrophilic petrolatum have been found acceptable, although it is felt that the ability of DMSO to penetrate the skin may have an adverse effect on treatment. The following concentrations are preferred:

|                | Concentration[1] Range |
|----------------|-----------------------|
| Preferred      | 0.1 to 10%            |
| More Preferred | 0.1 to 5%             |
| Most Preferred | 0.3 to 5%             |

[1] Weight percent N—trialkylsilyl-6-aminonicotinamide in base.

The therapeutic compositions are applied topically to the affected area of the skin.

3. Examples

The following examples are illustrative of the synthesis of the substituted 6-aminonicotinamides of the present invention, and of their utility in the topical treatment of psoriatic lesions. As will be obvious and understood, other compounds within the scope of this invention may be formed by selecting appropriate reactants and quantities. Thus, the examples provided should not be construed as limiting the scope of the invention.

The following abbreviations have been adopted for use in the examples: 6-AN (6-aminonicotinamide); DMF (dimethylformamide); $Et_3N$ (triethylamine); $Et_3SiCl$ (triethyl chlorosilane); BSA [bis(trimethylsilyl)acetamide]

3a. Preparation of bis-trimethylsilyl-6-aminonicotinamide 0.51 g of 6-AN was stirred with 3.28 g (4 equivalents) of BSA for one hour at room temperature in a reaction flask. No reaction was observed. Thereafter, 1 ml of DMF was added and the mixture stirred for several days, after which time the 6-AN had gone into solution. The mixture was then transferred to a rotary evaporator connected to a high-vacuum pump, with two dry-ice traps. The reaction flask was gradually heated to 90° C. and after 4 hours, the residue in the flask had crystallized, while a portion of the crystal had sublimed on the upper portions of the flask.

The product was scraped from the walls of the flask and the fraction that had sublimed, an intermediate fraction that was mostly sublimed and the crystalline residue, were isolated. In all three cases, the structure of the product was found to be

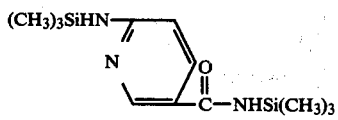

and confirmed by NMR spectroscopy.

3b. Preparation of bis-triethylsilyl-6-aminonicotinamide 2.06 grams (15 m moles) of 6-AN and 35 ml dry DMF were added to a 250 ml flask and heated under Argon until the 6-AN dissolved. After cooling, but while the mixture was still warm, 25 ml (180 m moles) of $Et_3N$ was added to form a cloudy solution which was cooled in dry ice. After 10 minutes, 15 ml of $Et_3SiCl$ was added and the mixture kept in the dry ice for an additional 30 minutes. The mixture was left overnight at room temperature.

A filter, flask and funnel were dried under vacuum at 120° C. for 2 hours. The slightly yellow reaction mixture was filtered through medium sintered glass in a glovebox, rinsed one time with 10 mls of toluene, and stripped to dryness on a rotovap for one hour. Forty mls of toluene and 5 mls $Et_3N$ were added to dissolve oils. The resulting solution was filtered through GF/F in a glovebox and stripped ty dryness at 90° C. for one hour at 0.3 torr. 5.06 grams of product (confirmed to be bis-triethylsilyl-6-aminonicotinamide by NMR) were recovered (theoretical = 5.46).

3c. Preparation of bis-t-butylsilyl-6-aminonicotinamide 2.00 grams (14.58 m moles) of 6-AN and 40 mls dry DMF were added to a 100 ml flask and heated under argon until the 6-AN dissolved. After cooling to room temperature, 22 ml (158 m moles) of $Et_3N$ was added to form a first clear, then cloudy solution. Just before it became very cloudy, 13.6 grams of t-butyl dimethylsilylchloride was added, causing instant precipitation. The mixture was left overnight at room temperature.

The next morning, the reaction mixture was almost pure white, with a trace of yellow. Toluene (20 ml) was added and the mixture cooled in dry ice to approximately 0° C. After cooling, the mixture was filtered through medium sintered glass and stripped in a rotovap. Yield of desired product (confirmed by NMR) was 5.34 grams (theoretical = 5.33 grams).

3d. Therapeutic Examples

The following examples are illustrative of formulations of compositions according to this invention. Although the examples utilize a named compound, the examples are not intended to be limited to the specific compound named, but any member of the above-described group of compounds or combination thereof could be substituted therefor within the scope of this invention.

TABLE 1

| PATIENT | AREA AFFECTED | BASE | CONCENTRATION[1] | RESULTS |
|---|---|---|---|---|
| 1 | First dorsum of the fifth finger | DMSO | 3% | Slight improvement in 4th week. |
| 2 | Medium size plaque below right knee | A | 1% | Lesion cleared completely within 4 weeks, although slight reoccurrence during 5th week. |
| 3 | Plaque right forearm | DMSO[2] Corn Oil[2] | 1% | Mostly cleared in 3 weeks, complete clearing after discontinued treatment. |
|   | Plaque lower right forearm | A | 1% | No improvement after 5 weeks |
| 4 | Plaque below right knee | DMSO | 0.5% | Complete clearing after one week; treatment then terminated and some recurrence after 5 weeks. |

TABLE 1-continued

| PA-TIENT | AREA AFFECTED | BASE | CONCENTRATION[1] | RESULTS |
|---|---|---|---|---|
| 5 | Large plaque on left forearm | DMSO | 3% | Fifty percent improvement after 2 weeks with almost complete clearing after 4 weeks. |

[1]Weight percent.
[2]Treatment began with DMSO base, after 3 weeks base switched to corn oil. The corn oil base caused irritation.

Referring to Table 1, the effectiveness of the composition of the present invention in treating patients with psoriasis is illustrated. Bis-trimethylsilyl-6-aminonotinamide in varying concentrations in a base of either dimethyl sulfoxide (DMSO) or hydrophilic petrolatum (A). The particular hydrophilic petrolatum employed was obtained from Beiersdorf, Norwalk, Connecticut, under the tradename "Aquaphor" (A). No adverse side effects were observed in any of the treatments, aside from minor irritation when a corn oil base was tried.

Although the best mode contemplated for carrying out the present invention has been herein shhown and described, it will be appreciated that variations and modifications may be made without departing from what is regarded to be the subject matter of the present invention.

What is claimed is:

1. A method for alleviating the symptoms of psoriasis in a human suffering therefrom, comprising applying a N-trialkylsilyl-6-aminonicotinamide at a concentration from 0.01 to 10% by weight in a carrier material to the affected area of skin.

2. The method of claim 1, wherein the concentration of the N-trialkylsilyl-6-aminonicotinamide is in the range from 0.01 to 5 weight percent.

3. A method of claim 1 or 2, wherein the N-trialkylsilyl-6-aminonicotinamide is bis-trimethylsilyl-6-aminonicotinamide.

4. A method of claim 1 or 2, wherein the N-trialkylsilyl-6-aminonicotinamide is bis-triethylsilyl-6-aminonicotinamide.

5. A method of claim 1 or 2, wherein the N-trialkylsilyl-6-aminonicotinamide is bis-t-butylsilyl-6-aminonicotinamide.

6. A therapeutic composition for relieving the symptoms of psoriasis, said composition including a N-trialkylsilyl-6-aminonicotinamide present in a carrier material at a concentration in the range from 0.01 to 10 weight percent.

7. A therapeutic composition as in claim 6, wherein the concentration of the composition is in the range from 0.01 to 5 weight percent.

8. A therapeutic composition as in either claim 6 or 7, wherein the carrier material is selected from the group conisting of a cream, an ointment and a lotion.

9. A therapeutic composition, as in either claim 6 or 7, wherein the carrier material is selected from the group consisting of dimethyl sulfoxide and hydrophilic petrolatum.